US00PP33594P2

(12) United States Plant Patent
Krebs

(10) Patent No.: US PP33,594 P2
(45) Date of Patent: Nov. 2, 2021

(54) ***RHODODENDRON* PLANT NAMED 'HOLDENRHODO201'**

(50) Latin Name: *Rhododendron hybrida*
Varietal Denomination: HoldenRhodo201

(71) Applicant: Holden Forests and Gardens, Kirtland, OH (US)

(72) Inventor: Stephen Krebs, Painesville, OH (US)

(73) Assignee: HOLDEN FORESTS AND GARDENS, Kirtland, OH (US)

( * ) Notice: Subject to any disclaimer, the term of this patent is extended or adjusted under 35 U.S.C. 154(b) by 0 days.

(21) Appl. No.: 17/063,876

(22) Filed: Oct. 6, 2020

(51) Int. Cl.
*A01H 5/02* (2018.01)
*A01H 6/36* (2018.01)

(52) U.S. Cl.
USPC ..... Plt./238
CPC ..... *A01H 6/364* (2018.05)

(58) Field of Classification Search
USPC ..... Plt./238, 239
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of hybrid *Rhododendron* plant named 'HoldenRhodo201' that is characterized by its showy flowers with strong marginal undulation, its flowers that are pink, fading to white and have a deep red flare, its profuse and consistent flowering with flower buds that are hardy to at least −15° F., its compact plant habit, its foliage that is glossy and dark in color, its ease of propagation by stem cuttings, its vigorous growth habit in full sun in unamended sand and gravel loam soils up to pH 6.2, and its high resistance to root rot caused by *Phytophthora cinnamomi*.

2 Drawing Sheets

Botanical classification: *Rhododendron hybrida*.
Cultivar designation: 'HoldenRhodo201'.

BACKGROUND OF THE INVENTION

The present invention relates to a new and distinct cultivar of *Rhododendron* plant of hybrid origin, botanically known as *Rhododendron* 'HoldenRhodo201' and will be referred to hereafter by its cultivar name, 'HoldenRhodo201'. 'HoldenRhodo201' is a new cultivar of *Rhododendron* shrub grown for use as a landscape plant.

The new cultivar arose from a controlled breeding program by the Inventor in Madison, Ohio with the objective of developing a new cultivar of *Rhododendron* with resistance to root rot caused by *Phytophthora cinnamomi*, flower bud and plant hardiness in U.S.D.A. Zone 5, and a compact growth habit.

The new cultivar was derived from a cross made by the Inventor in 2000 between *Rhododendron* 'Ingrid Mehlquist' (not patented) as the female parent, and *Rhododendron* 'Rio' (not patented) as the male parent. The Inventor selected 'HoldenRhodo201' as a single unique plant amongst the seedlings that resulted from the above cross in 2007.

Asexual propagation of the new cultivar was first accomplished by semi-hardwood stem cuttings in Madison, Ohio, in fall of 2007 by the Inventor. Asexual propagation by semi-hardwood stem cuttings and tissue culture utilizing meristematic tissue has determined that the characteristics of the new cultivar are stable and are reproduced true to type in successive generations.

SUMMARY OF THE INVENTION

The following traits have been repeatedly observed and represent the characteristics 'HoldenRhodo201'. These attributes in combination distinguish 'HoldenRhodo201' as a new and distinct cultivar of *Rhododendron*.

1. 'HoldenRhodo201' exhibits showy flowers with strong marginal undulation.
2. 'HoldenRhodo201' exhibits flowers that are pink, fading to white and have a deep red flare.
3. 'HoldenRhodo201' exhibits profuse and consistent flowering with flower buds that are hardy to at least −15° F.
4. 'HoldenRhodo201' exhibits a compact plant habit.
5. 'HoldenRhodo201' exhibits foliage that is glossy and dark in color.
6. 'HoldenRhodo201' exhibits ease of propagation by stem cuttings.
7. 'HoldenRhodo201' exhibits a vigorous growth habit in full sun in unamended sand and gravel loam soils up to pH 6.2.
8. 'HoldenRhodo201' exhibits high resistance to root rot caused by *Phytophthora cinnamomi*.

The female parent of 'HoldenRhodo201' differs from 'HoldenRhodo201' in having a much smaller inflorescence size and less pronounced flares on the flower petals. The male parent of 'HoldenRhodo201' differs from 'HoldenRhodo201' in having a much less compact growth habit, leaves that are larger in size and less glossy, more susceptibility to root rot caused by *Phytophthora cinnamomi*, and flowers that remain pink in color and lack a red flare. 'HoldenRhodo201' can also be most closely compared to the *Rhododendron* cultivars 'Mardi Gras' (not patented) and 'Besse Howells' (not patented). 'Mardi Gras' is similar to 'HoldenRhodo201' in having a compact habit and flowers that fade from pink to white in color. 'Mardi Gras' differs from 'HoldenRhodo201' in having flower buds that are less hardy (U.S.D.A. Zone 6) and conspicuous pubescent hairs on the foliage. 'Besse Howells' is similar to 'HoldenRhodo201' in having inflorescences that are large in size and cold hardiness to U.S.D.A. Zone 5. 'Besse Howells' differs from 'HoldenRhodo201' in having a much less compact plant habit, more susceptibility to root rot caused by *Phytophthora cinnamomi*, and inflorescences that are rose-purple in color.

BRIEF DESCRIPTION OF THE DRAWINGS

The accompanying colored photographs were taken of the new cultivar as grown in Madison, Ohio.

The photograph in FIG. 1 was taken of a plant 10 years in age as grown in the ground of 'HoldenRhodo201' in bloom.

Figure 1:
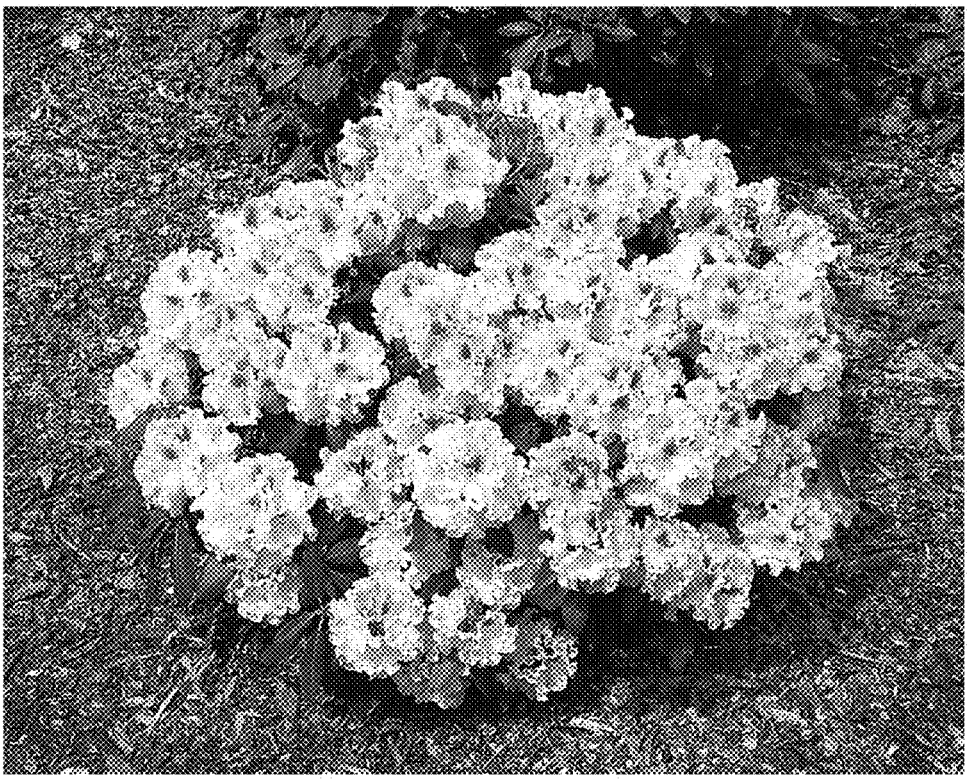
Figure 2:
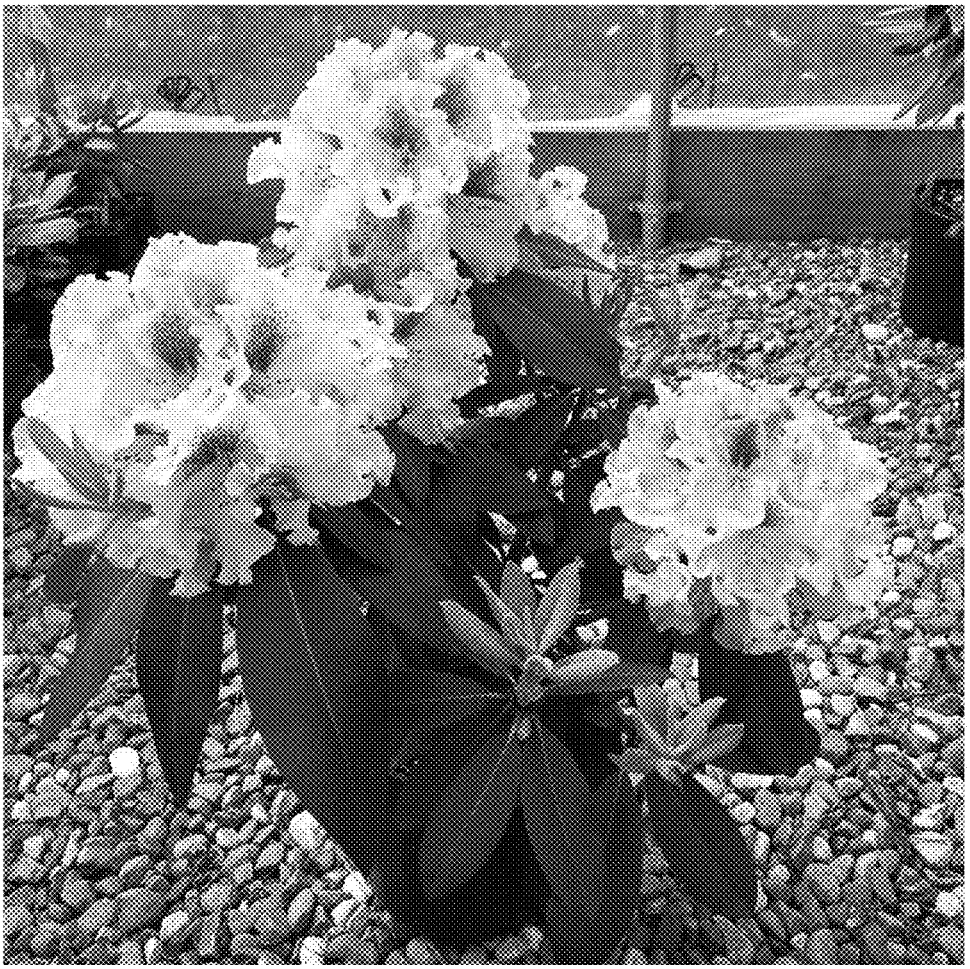

The photograph in FIG. 2 was taken of a plant 2.5 years in age as grown in a 2-gallon container in a poly-greenhouse and provides a close-up view of the inflorescences of HoldenRhodo201'.

The colors in the photographs are as close as possible with the digital photography and printing techniques utilized and the color codes in the detailed botanical description accurately describe the new *Rhododendron*.

DETAILED BOTANICAL DESCRIPTION OF THE PLANT

The following is a detailed description of 11-year-old plant of the new cultivar as grown outdoors in the ground in Madison, Ohio. The phenotype of the new cultivar may vary with variations in environmental, climatic, and cultural conditions, as it has not been tested under all possible environmental conditions. The color determination is in accordance with The 1995 Colour Chart of The Royal Horticultural Society, London, England, except where general color terms of ordinary dictionary significance are used.

General characteristics:

*Blooming period.*—Average of 2 to 3 weeks beginning in mid-May in Ohio.

*Plant type.*—Evergreen shrub.

*Plant habit.*—Rounded, compact and densely branched.

*Height and spread.*—An 11-year-old plant reaches 99 cm in height and 165 cm in width as a mature plant in the landscape.

*Cold hardiness.*—Plant is hardy to at least U.S.D.A. Zone 5, flower buds that are hardy to at least −15° F.

*Diseases and pests.*—Resistance to root rot caused by *Phytophthora cinnamomi*, no susceptibility or resistance to pests has been observed.

*Root description.*—Fibrous and a blend of 164B and 166C in color.

*Propagation.*—Tissue culture (preferred) or semi-hardwood stem cuttings.

*Growth rate.*—Moderate.

*Root development.*—8 to 10 weeks for root initiation and 2 years to produce a young plant from a rooted cutting.

Stem description:

*Shape.*—Round.

*Stem color.*—Young growth; 143C, transitioning to 144A during the growing season, as the plant goes dormant, another transition occurs changing to 163B before eventually becoming a blend of 197A and 197B with some flushes of 175C at maturity.

*Stem size.*—Main stem an average of 5 cm in height and 6.5 cm in width, lateral stems an average of 34 cm in length and 5.5 cm in width at the base where they branch from the main stem and 6 mm in width near the terminal end.

*Stem surface.*—Young stems; slightly rough to the touch, lightly covered with rough pubescent hairs; less than 1 mm in length and 163B in color, remaining rough to touch in summer with hair color changing to 200B, mature stems and wood; somewhat rough, dull and glabrous.

*Stem aspect.*—Stems angled at 45° near the base of the shrub, becoming nearly vertical near the top.

*Stem strength.*—Strong.

*Branching.*—Densely branched, an average of 6 lateral branches branching off main stem.

Foliage description:

*Leaf shape.*—Elliptic.

*Leaf division.*—Simple.

*Leaf base.*—Rounded to cuneate.

*Leaf apex.*—Acute.

*Leaf margins.*—Entire.

*Leaf venation.*—Pinnate off the midrib and reticulate between the pinnae, upper surface color; midrib 154B in color with lateral vein color matching mid-rib coloration, lower surface color; midrib and lateral veins 150C in color with granular hairs on midrib 200C in color.

*Leaf attachment.*—Petiolate.

*Leaf arrangement.*—Alternate.

*Leaf internode length.*—0.1 cm to 9.6 cm becoming progressively smaller from base to apex of shoot, 0.1 to 0.2 cm in whorl of foliage at shoot apex.

*Leaf orientation.*—Held mostly parallel to the ground, some angled 30° above parallel.

*Leaf aspect.*—Flat but cupping downward at the apex, moderate twisting on some leaves.

*Leaf surface.*—Upper surface; smooth, glossy, and covered with granular-pubescent (especially when young) with a thick texture, granular-pubescence 155C in color, lower surface; smooth, dull, and glabrous except the prominent mid-rib with similar granular-pubescence described in upper leaf surface.

*Leaf color.*—Young leaves upper surface; 144A, young leaves lower surface; 144C, mature leaves upper surface; 147A, mature leaves lower surface; 146C.

*Leaf size.*—4.0 cm to 15.5 cm in length and 1.2 cm to 5.0 cm in width.

*Leaf quantity.*—An average of 7 leaves per lateral branch 10.6 cm length.

*Petioles.*—Average of 1.6 cm in length and 2 to 3.5 mm in diameter, both surfaces 144C in color and are covered with a granular-pubescence.

Flower description:

*Inflorescence type.*—Raceme.

*Lastingness of flowers.*—Individual flowers last 2 to 4 days, total duration of bloom ranges from 2 to 3 weeks, self-cleaning.

*Inflorescence size.*—Average of 13.3 cm in height and 14.7 cm in width.

*Flower size.*—An average of 10.2 cm in depth and 9 cm in diameter.

*Flower fragrance.*—Not noticeably fragrant.

*Flower shape.*—Broad, tubular funnel.

*Flower number.*—Range of 13 to 18 per inflorescence.

*Flower aspect.*—Outward.

*Flower bud.*—Obovate to elliptic in shape, round in cross-section, pointed apex, an average of 3.3 cm in length and 1.8 cm in diameter, 144B in color on the margins of each bud scale, 147B toward the center of the scales, 165A at the apex of each bud scale and the bud, average of 3.4 cm in length, 1.9 cm in diameter, pointed apex, round in cross-section.

*Flower attachment.*—Pedicellate.

*Petal number.*—5.

*Petal shape.*—Ovate to elliptic.

*Petal color.*—Expanding flowers buds (balloon stage) 66D in color, when first opening inner surface; 69C in the center and flushes to 63C toward margins, the uppermost central petal has linear speckles 60A, when first opening outer surface; 73B, when fully open inner surface; 69C with linear speckles 60A, when fully open lower surface; 69B, speckles 60A, fading to 69D, speckles do not fade.

*Petal surface.*—Smooth, glabrous along the interior and exterior surfaces.

*Petal margins.*—Entire, strongly undulate.

*Petal apex.*—Acuminate to obtuse, often undulate and slightly recurved.

*Petal base.*—Truncate and fused.

*Petal size.*—An average of 2.7 cm in length and 1.7 cm in width.

*Sepal number.*—Average of 5.

*Sepal shape.*—Narrowly deltate.

*Sepal margin.*—Entire.

*Sepal size.*—Average of 0.2 cm in length and 0.4 cm in width.

*Sepal surface.*—Both surfaces covered with granular-pubescence, 155C in color.

*Sepal apex.*—Acuminate.

*Sepal base.*—Fused.

*Sepal color.*—Interior surface; not visible, enclosing base of the corolla tube, immature and mature exterior surface; 150C in color.

*Calyx.*—Shallowly cup-shaped an average of 1.5 mm in length and 5 mm in diameter, with individual sepals separated by rounded sinuses.

*Pedicels.*—An average of 2.5 cm in length and 0.2 cm in diameter, 150B in color, covered with rough, granular-pubescence 155C in color.

Reproductive organs:

*Gynoecium.*—Pistil; 1, stigmas; round in shape, 61A in color, 2 mm in diameter, style; average 3.8 cm in length, 68D in color, ovary; 144C in color.

*Androecium.*—Stamens; typically 10, anthers; oblong to elliptical in shape, average of 2.8 mm in length and 0.1 cm width, 154D in color, pollen not observed.

*Fruit/seeds.*—Dehiscent, 5-valved capsule with an average of 7 mm length and 4 mm in width, 144A in color, seed; no seed production observed.

It is claimed:

1. A new and distinct cultivar of *Rhododendron* plant named 'HoldenRhodo201' as herein illustrated and described.

* * * * *